US006699684B2

(12) United States Patent
Ho et al.

(10) Patent No.: US 6,699,684 B2
(45) Date of Patent: *Mar. 2, 2004

(54) METHOD OF MONITORING BIOFOULING IN MEMBRANE SEPARATION SYSTEMS

(75) Inventors: Bosco P. Ho, Wheaton, IL (US); May W. Wu, Lisle, IL (US); E. H. Kelle Zeiher, Naperville, IL (US); Mita Chattoraj, Warrenville, IL (US)

(73) Assignee: Nalco Company, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/201,088

(22) Filed: Jul. 23, 2002

(65) Prior Publication Data

US 2004/0018583 A1 Jan. 29, 2004

(51) Int. Cl.[7] .............................. A01N 1/00; A01N 1/02
(52) U.S. Cl. .............................. 435/29; 435/4; 435/968
(58) Field of Search .............................. 435/4, 29, 968

(56) References Cited

U.S. PATENT DOCUMENTS

| 4,783,314 A | 11/1988 | Hoots et al. ............. 422/3 |
| 4,992,380 A | 2/1991 | Moriarty et al. ............. 436/55 |
| 5,041,386 A | 8/1991 | Pierce et al. ............. 436/50 |
| 5,320,967 A | 6/1994 | Avallone et al. ............. 436/50 |
| 5,416,323 A | 5/1995 | Hoots et al. ............. 250/302 |
| 5,714,387 A | 2/1998 | Fowee et al. ............. 436/27 |
| 6,329,165 B1 | 12/2001 | Chattoraj et al. ............. 435/29 |

FOREIGN PATENT DOCUMENTS

JP   10-282410   4/2000

OTHER PUBLICATIONS

Ridgeway, H. F., Ph. D. and H. Flemming, "Membrane Biofouling", *Water Treatment Membrane Processes*, McGraw Hill, 1996, pp. 6.1 to 6.62.

Osmonics, The Filtration Spectrum, Copyright 1998 by Osmonics, Inc. Minnetonka, Minnesota, USA.

Corporate Headquarters, 5951 Clearwater Drive, Minnetonka, Minnesota 55343–8995 USA.

*Primary Examiner*—Jon P. Weber
(74) *Attorney, Agent, or Firm*—Margaret M. Brumm; Thomas M. Breininger

(57) ABSTRACT

Methods for monitoring and/or controlling biofouling in membrane separation systems are provided. The present invention utilizes measurable amounts of fluorogenic agent(s) added to a feed stream to monitor and/or control the level of microbial growth during membrane separation and, thus, the purification of such feed stream during membrane separation.

19 Claims, No Drawings

METHOD OF MONITORING BIOFOULING IN MEMBRANE SEPARATION SYSTEMS

FIELD OF THE INVENTION

The present invention relates generally to membrane separation and, more particularly, to methods for monitoring and/or controlling biofouling in membrane separation systems.

BACKGROUND OF THE INVENTION

Membrane separation, which uses a selective membrane, is a fairly recent addition to the industrial separation technology for processing of liquid streams, such as water purification. In membrane separation, constituents of the influent typically pass through the membrane as a result of a driving force(s) in one effluent stream, thus leaving behind some portion of the original constituents in a second stream. Membrane separations commonly used for water purification or other liquid processing include microfiltration (MF), ultrafiltration (UF), nanofiltration (NF), reverse osmosis (RO), electrodialysis, electrodeionization, pervaporation, membrane extraction, membrane distillation, membrane stripping, membrane aeration, and other processes. The driving force of the separation depends on the type of the membrane separation. Pressure-driven membrane filtration, also known as membrane filtration, includes microfiltration, ultrafiltration, nanofiltration and reverse osmosis, and uses pressure as the driving force, whereas the electrical driving force is used in electrodialysis and electrodeionization. Historically, membrane separation processes or systems were not considered cost effective for water treatment due to the adverse impacts that membrane scaling, membrane fouling, membrane degradation and the like had on the efficiency of removing solutes from aqueous water streams. However, advancements in technology have now made membrane separation a more commercially viable technology for treating aqueous feed streams suitable for use in industrial processes.

Furthermore, membrane separation processes have also been made more practical for industrial use, particularly for raw and wastewater purification. This has been achieved through the use of improved diagnostic tools or techniques for evaluating and monitoring membrane separation performance. The performance of membrane separation, such as efficiency (e.g. flux, membrane permeability, permeate recovery, energy efficiency, time between membrane cleanings or time to conduct a cleaning cycle) and effectiveness (e.g. rejection or selectivity) are typically reduced by membrane fouling.

Membrane separation processes are prone to fouling by microbes, i.e. biofouling. The growth of microorganisms during membrane separation is a constant concern particularly in aqueous streams which provide optimum conditions for microbial growth. Biofouling is particularly detrimental to membrane separation systems because once it is started, the growth rate accelerates and biofouling can facilitate other types of fouling as well. For example, the exopolymeric substances ("EPS") or slime layer of the biomass can trap and hold scales and other particulates that might otherwise pass out of the membrane separation system during operation. Furthermore, a thick EPS layer can also decrease turbulent flow within the membrane. This can lead to an increase in the concentration polarization layer which is a known contributor to membrane scaling phenomena.

The immediate and most obvious effect of biofouling is a decrease in membrane permeate output and/or a rise in the pressure drop along the length of a membrane element on the feed and concentrate side of the membrane, referred to herein as "differential pressure." Under a constant pressure, this results in a loss in the production of permeate. Pressure can be increased in order to maintain a constant flux, but this increases energy consumption and further accelerates fouling. In addition, continued operation under these conditions (i.e., a loss of permeate flux, an increase in pressure differential and an increase in the pressure driving force) would necessarily require an increased number of cleanings over the life time of the membrane, thereby decreasing the membrane life and potentially increasing water costs if a significant amount of down time is required due to the cleanings. Less obvious effects include reduced solute rejection, contamination of permeate and deterioration of membrane modules, such as biodegradation on membrane glue lines. The review article written by H. F. Ridgway & H. Flemming entitled "Membrane Biofouling" and appearing in *Water Treatment Membrane Processes*, McGraw Hill, pp. 6.1 to 6.62, 1996, is incorporated herein by reference.

In general, biofouling is controlled through the use of biocides and other biocontrol agents, i.e., chemicals that can inhibit microbial growth by destroying the cell wall or cellular constituents of microorganisms. Mechanical means and radiation means are additional possibilities. Intermittent use of biocides is typically encouraged since biocides can be both expensive and toxic. Thus, to prevent waste, constant monitoring and testing of the water system and of the membrane process parameters are required to determine the proper quantity of biocide for controlling microbial growth.

However, known monitoring techniques may not provide an adequate level of sensitivity, specificity and/or accuracy with respect to monitoring the effects of biofouling on membrane separation. Typical monitoring techniques include pressure and flow measurements and grab sampling to determine microbial population. With respect to pressure measurements, monitoring is generally conducted by evaluating changes in the differential pressure along the length of the membrane. With respect to flow measurement, the flow meters generally employed in such systems are subject to calibration inaccuracies, thus requiring frequent calibration. However, the changes in pressure and flow are not necessarily specific to biofouling, as they can be influenced by any suitable increase in scalants, foulants and/or like constituents that can build-up and remain in the system during membrane separation. As previously discussed, the microbial growth layer can enhance other types of fouling since it can trap or hold scales and other particulates that might otherwise pass out of the system during membrane separation.

For grab samples, water samples are typically taken from the feed stream and/or from the exit stream. Samples from the permeate stream can also be taken to determine if there is any contamination in the permeate. A typical technique involves withdrawing a sample, diluting the sample, and applying the sample to the surface of a nutrient agar medium. After incubation for 24 to 28 hours, the sample is checked for the presence of microorganisms and, where appropriate, the organisms are counted by manual or video means. A variation on this method includes withdrawing a sample and culturing it for a predetermined time, and then observing the culture medium by nephelometry or turbidimetry. In other words, the presence of microorganisms is revealed by the opacity of the culture medium.

A significant problem associated with grab sampling is the time lag between withdrawing the sample and completing the analysis to determine the level of microbiological activity in the sample. In this regard, the time lag can be exacerbated when the samples have to be transported off-site for analysis which can further delay obtaining the results.

Another problem associated with grab sampling is that it can underestimate the overall microbiological activity in the industrial water system because grab sampling is only sufficient to provide an indication of the planktonic microbiological activity, not the sessile activity. Planktonic microbiological populations are alive and exist suspended within the water of a water system. As used herein, the term "sessile" refers to populations of microorganisms that are alive, but immobile. It is possible to get an industry-acceptable measurement of planktonic populations by grab sampling since planktonic microorganisms are suspended within the water sample that is removed and tested for microorganism concentrations. In contrast, sessile populations are strongly attached to the structures within the system and their presence is not easily measured by removing a sample of water and testing this sample for microorganisms. In this regard, the level of planktonic cells may not directly correlate to the level of sessile cells in the membrane separation system.

Accordingly, a need exists to monitor and/or control biofouling in membrane separation systems in real-time where conventional monitoring techniques are generally complex and/or may lack the sensitivity, specificity and/or accuracy necessary to adequately monitor biofouling such that membrane separation performance can be optimized.

SUMMARY OF THE INVENTION

The present invention provides methods for monitoring and/or controlling biofouling in membrane separation systems capable of treating feed streams suitable for use in industrial processes. In this regard, the use of a fluorogenic agent can be utilized to monitor the growth of microorganisms during membrane separation (i.e., monitor biofouling). Applicants have discovered that the fluorescent monitoring technique of the present invention can be performed with a high degree of sensitivity, specificity and/or accuracy with respect to the detection of biofouling, such that membrane separation performance and efficiency can be controllably optimized.

To this end, in an embodiment of the present invention, a method of monitoring biofouling in a membrane separation system including a membrane capable of separating a feed stream into at least a first stream and a second stream is provided. The method includes the steps of providing a fluorogenic agent; adding the fluorogenic agent to the feed stream; providing a fluorometer to detect the fluorescent signal of the fluorogenic agent in at least one of the feed stream, the first stream and the second stream; reacting the fluorogenic agent with one or more microorganisms within the membrane separation system; forming a reacted fluorogenic agent; using the fluorometer to measure the fluorescent signal of at least one of the fluorogenic agent and the reacted fluorogenic agent in at least one of the first stream and the second stream and optionally the feed stream; and monitoring biofouling in the membrane separation system based on the change in the signal of the fluorogenic agent, or the reacted fluorogenic agent or a combination of both signals measured.

It is, therefore, an advantage of the present invention to provide methods that utilize a fluorogenic agent to monitor and/or control biofouling in membrane separation systems.

Another advantage of the present invention is to provide methods that utilize the monitoring of fluorogenic agents to improve the performance of membrane separation.

A further advantage of the present invention is to provide methods for monitoring microbial growth with selectivity, specificity and/or accuracy based on the monitoring of the fluorogenic agent added to the membrane separation system.

Yet another advantage of the present invention is to provide a control signal to add biocides or biocontrol agents to reduce the biofouling in membrane separation systems.

Still further an advantage of the present invention is to provide methods for monitoring the effectiveness of cleaning agents, biocides and biocontrol agents to reduce cleaning time and increase time between cleanings.

Additional features and advantages of the present invention are described in, and will be apparent in, the detailed description of the presently preferred embodiments.

DETAILED DESCRIPTION OF THE PRESENTLY PREFERRED EMBODIMENTS

The present invention provides methods for monitoring and/or controlling biofouling in membrane separation systems that are capable of removing solutes and/or other impurities from feed streams, such as aqueous feed streams, which are suitable for use in a number of different industrial applications. More specifically, the methods of the present invention can monitor and/or control biofouling in membrane separation systems based on monitoring the activity of a fluorogenic agent(s) which has been added to the feed stream. In this regard, biofouling due to microbial growth during membrane separation can be evaluated with a high degree of selectivity, specificity and accuracy such that the performance of the membrane separation system can be effectively optimized.

The methods of the present invention can include a variety of different and suitable components, process steps, operating conditions and the like, for monitoring and/or controlling biofouling in membrane separation systems. In an embodiment, the membrane separation system of the present invention includes cross-flow and dead-end flow systems. During cross-flow membrane separation systems, the feed stream can be treated in a flow direction that is substantially parallel to the membrane of the separation system. With respect to dead-end flow systems, the feed stream can be treated in a flow direction that is substantially perpendicular to the membrane of the separation system.

In general, the membrane separation systems of the present invention are capable of treating or purifying feed streams by dividing the feed stream into separate streams. In an embodiment, the feed stream is separated into at least a first and second stream, such as a permeate stream and a concentrate stream. The feed stream can contain various solutes, such as dissolved organics, dissolved inorganics, dissolved solids, suspended solids, the like or combinations thereof. Upon separation of the feed stream into the permeate and the concentrate, in membrane filters for example, the permeate stream essentially contains a substantially lower concentration of dissolved and/or suspended solutes as compared to the aqueous feed stream. On the other hand, the concentrate stream has a higher concentration of dissolved and/or suspended solutes as compared to the aqueous stream. In this regard, the permeate represents a purified feed stream, such as a purified aqueous feed stream.

It should be appreciated that the present invention can be utilized with respect to a number of different types of membrane separation systems including, for example, cross-flow systems, dead-end flow systems, reverse osmosis, nanofiltration, ultrafiltration, microfiltration, electrodialysis, electrodeionization, pervaporation, membrane extraction, membrane distillation, membrane stripping, membrane aeration and the like or combinations thereof. Reverse osmosis, nanofiltration, ultrafiltration and microfiltration are the preferred membrane separation systems.

In reverse osmosis, the feed stream is typically processed under cross-flow conditions. In this regard, the feed stream flows substantially parallel to the membrane surface such that only a portion of the feed stream diffuses through the membrane as permeate. The cross-flow rate is routinely high in order to provide a scouring action that lessens membrane surface fouling. This can also decrease concentration polarization effects (e.g., concentration of solutes in the reduced-turbulence boundary layer at the membrane surface, which can increase the osmotic pressure at the membrane and thus can reduce permeate flow). The concentration polarization effects can inhibit the feed stream water from passing through the membrane as permeate, thus decreasing the recovery ratio, e.g., the ratio of permeate to applied feed stream.

Reverse osmosis systems can employ a variety of different types of membranes. Such commercial membrane element types include, without limitation, hollow fiber membrane elements, tubular membrane elements, spiral-wound membrane elements, plate and frame membrane elements, and the like, some of which are described in more detail in "The Nalco Water Handbook," Second Edition, Frank N. Kemmer ed., McGraw-Hill Book Company, New York, N.Y., 1988, incorporated hereinto, particularly Chapter 15 entitled "Membrane Separation". It should be appreciated that a single membrane element may be used in a given membrane filtration system, but a number of membrane elements can also be used depending on the industrial application.

A typical reverse osmosis system is described as an example of membrane filtration and more generally membrane separation. Reverse osmosis uses mainly spiral wound elements or modules, which are constructed by winding layers of semi-permeable membranes with feed spacers and permeate water carriers around a central perforated permeate collection tube. Typically, the modules are sealed with tape and/or fiberglass over-wrap. The resulting construction has one channel which can receive an inlet flow. The inlet stream flows longitudinally along the membrane module and exits the other end as a concentrate stream. Within the module, water passes through the semi-porous membrane and is trapped in a permeate channel which flows to a central collection tube. From this tube it flows out of a designated channel and is collected.

In practice, membrane modules are stacked together, end to end, with inter-connectors joining the permeate tubes of the first module to the permeate tube of the second module, and so on. These membrane module stacks are housed in pressure vessels. Within the pressure vessel feed water passes into the first module in the stack, which removes a portion of the water as permeate water. The concentrate stream from the first membrane becomes the feed stream of the second membrane and so on down the stack. The permeate streams from all of the membranes in the stack are collected in the joined permeate tubes.

Within most reverse osmosis systems, pressure vessels are arranged in either "stages" or "passes." In a staged membrane system, the combined concentrate streams from a bank of pressure vessels are directed to a second bank of pressure vessels where they become the feed stream for the second stage. Commonly systems have 2 to 3 stages with successively fewer pressure vessels in each stage. For example, a system may contain 4 pressure vessels in a first stage, the concentrate streams of which feed 2 pressure vessels in a second stage, the concentrate streams of which in turn feed 1 pressure vessel in the third stage. This is designated as a "4:2:1" array. In a staged membrane configuration, the combined permeate streams from all pressure vessels in all stages are collected and used without further membrane treatment. Multi-stage systems are used when large volumes of purified water are required, for example for boiler feed water. The permeate streams from the membrane system may be further purified by ion exchange or other means.

In a multi-pass system, the permeate streams from each bank of pressure vessels are collected and used as the feed to the subsequent banks of pressure vessels. The concentrate streams from all pressure vessels are combined without further membrane treatment of each individual stream. Multi-pass systems are used when very high purity water is required, for example in the microelectronics or pharmaceutical industries.

It should be clear from the above examples that the concentrate stream of one stage of an RO system can be the feed stream of another stage. Likewise the permeate stream of a single pass of a multi-pass system may be the feed stream of a subsequent pass. A challenge in monitoring systems such as the reverse osmosis examples cited above is that there are a limited number of places where sampling and monitoring can occur, namely the feed, permeate and concentrate streams. In some, but not all, systems "inter-stage" sampling points allow sampling/monitoring of the first stage concentrate/second stage feed stream. Similar inter-pass sample points may be available on multi-pass systems as well.

In contrast to cross-flow filtration membrane separation systems, conventional filtration of suspended solids can be conducted by passing a feed fluid through a filter media or membrane in a substantially perpendicular direction. This effectively creates one exit stream during the service cycle. Periodically, the filter is backwashed by passing a clean fluid in a direction opposite to the feed, generating a backwash effluent containing species that have been retained by the filter. Thus conventional filtration produces a feed stream, a purified stream and a backwash stream. This type of membrane separation is typically referred to as dead-end flow separation and is typically limited to the separation of suspended particles greater than about one micron in size.

Cross-flow filtration techniques, on the other hand, can be used for removing smaller particles (generally about one micron in size or less), colloids and dissolved solutes. Such types of cross-flow membrane separation systems can include, for example, reverse osmosis, nanofiltration, ultrafiltration, microfiltration, electrodialysis or the like. Reverse osmosis can remove even low molecular weight dissolved species that are at least about 0.0001 to about 0.001 microns in minimum diameter, including, for example, ionic and nonionic species, low molecular weight molecules, water-soluble macromolecules or polymers, suspended solids, colloids, and such substances as bacteria and viruses.

In the conventional flow method of monitoring biofouling, the actual permeate flow rate is a direct reading from a flowmeter. However, the actual permeate flow rate can vary with respect to the feed stream temperature, the pressure driving force, feedstream solutes and suspended solids and, of course, the various fouling factors including biofouling. The normalized permeate flow is typically considered a more sensitive forecaster of trouble in a membrane separation system. Normalized permeate flow is determined through a simple calculation which eliminates the effect of actual system temperature and driving force variations and converts the actual permeate flow readings to what they would be if the system were operating at a standard ("normal") and constant pressure and temperature conditions, which are routinely the start-up driving force and a specified temperature such as 25° C. The calculation thus includes a temperature conversion factor and a pressure conversion factor for a given membrane, which are typically determined empirically with a new membrane or are provided by the membrane manufacturer. Another method, called the "clean water flux method" is used to measure the actual permeate flow using clean water at the standard pressure and temperature conditions. This method requires shutting down the operation and passing clean water through the system to determine fouling and is thus extremely inconvenient and time-consuming.

In the conventional differential pressure method of monitoring biofouling, the difference between two pressure measurements at two locations in the feed/concentrate stream is taken. Typical differential pressure will be the difference between the feed pressure and the concentrate pressure. It is a measure of the hydraulic pressure losses through the membrane-filtration membrane elements on the feed and concentrate side of the membrane and the associated manifold piping. In reverse osmosis, for example, another conventional preferred method is to measure the pressure differential on a single pressure vessel where biofouling is most likely to occur, i.e., the front membrane where the feed water enters. When the feed/concentrate flow channels become clogged, the driving force increases. The differential pressure also depends upon the feedstream flow rate and the percent recovery. An accurate comparison between differential pressure readings taken at different times requires that the membrane filtration system is operating at the same percent recovery and feed flow rate in each instance. In practice, the differential pressure reading is taken at some constant production parameter, such as constant permeate flow or constant pressure.

Another biofouling detection method is the destructive method of membrane autopsy. This includes, after cutting open a membrane removed from service, visual inspection of its surface, a membrane-surface microbiological analysis by swabbing the membrane surface, and surface analysis for deposits by SEM/EDS, IR, electron microscopy, ICP and like surface analysis techniques. By comparing the nature and relative quantities of the various compounds, elements and living organisms, a qualitative determination of biofouling versus other types of fouling and scaling can be determined.

Membrane separation systems and the monitoring thereof are unique because of the following considerations.

1. Systems are constructed with limited flexibility in terms of where monitoring may be done and/or where samples may be collected. Moreover, different types of fouling are usually located in specific segments of the membrane. For example, biofouling is usually predominant at the front end of the membrane system.

2. Membrane separation systems include a concentration polarization layer that forms as water is permeated through the barrier. This is not present in other water treatment systems, such as cooling water systems.

3. Because it is essential that the surface of the membrane remain clean, a relatively small amount of biofouling or fine precipitate can cause a significant performance loss. The performance loss in a membrane is, thus, more sensitive as compared to cooling water treatment. In this regard, performance loss in a membrane can occur at a film thickness appreciably lower than that required for heat transfer loss to occur in a cooling water system. Moreover, due to the small flow channels, the fouling, when not controlled or removed earlier, will continue to accelerate and it will be more difficult, if not impossible, to clean the membrane back to its original performance capability. A shortened membrane life is typically caused by this delay in detection of fouling.

4. The thin, semi-permeable films (polymeric, organic or inorganic) are sensitive to degradation by chemical species, including the chemicals secreted from the cell growth process and the cleaning chemicals. Products which contact membrane surfaces must be compatible with the membrane chemistry to avoid damaging the surface and thereby degrading performance.

5. Chemical treatments used in membrane systems must be demonstrated to be compatible with the membrane material prior to use. Damage from incompatible chemicals can result in immediate loss of performance and perhaps degradation of the membrane surface. Such immediate, irreversible damage from a chemical treatment is highly uncommon in cooling water systems.

6. In membrane separation systems, there is a continuous feed stream and at least one continuous discharge stream. The holding time of a membrane separation system is very short, i.e., on the order of a few seconds to a few minutes.

Based on these differences, a number of different factors and considerations must necessarily be taken into account when developing and/or implementing monitoring and controlling programs for biofouling as compared to other water treatment processes, such as cooling water treatment processes. For example, for effective use in membrane systems, it is believed that the fluorogenic agent must be able to respond to a much lower concentration of organisms than in other industrial water systems, including cooling water systems. In this regard, detection limits as low as about $10^4$ colony forming units per square centimeter ($cfu/cm^2$) are required when applied to membrane separation systems. At such low detection limits, the accuracy and reproducibility of the method are usually very poor.

The short holding time necessarily requires a fluorogenic agent that can react with speed and sensitivity to the microbial growth process under the limited holding time associated with membrane separation as compared to other industrial water systems, such as cooling water systems which have holding times typically of hours.

Due to the nature of a continuous feed stream with short residence time in the membrane separation system, the introduction of the fluorogenic agent is restricted to the feed stream and the measurement of the fluorogenic agent is restricted to the exit stream as the fluorogenic agent exits the system within minutes after its introduction. Thus, the membrane separation system provides an almost immediate measurement of biofouling after the introduction of the fluorogenic agent. The fluorogenic agent does not need to be further introduced until at a later time when the measurement is again deemed necessary.

As previously discussed, the methods of the present invention employ fluorogenic agents to monitor biofouling caused by microbial growth with a high degree of selectivity, sensitivity and/or accuracy such that the performance of membrane separation can be optimized. Microbiological organisms commonly found within industrial water systems which thus far have been detectable by and respond to the detection methods of the present process include, but are not limited to, Pseudomonas, Bacillus, Klebsiella, Enterobacter, Escherichia, Sphaerotilus and Haliscomenobacter.

It should be appreciated that the level of microbial activity during membrane separation is a function of different factors including the population of microbiological organisms in the feed stream, the amount of dissolved oxygen, temperature, water flow, the presence of microbial nutrients and the removal of microbial waste. Even in a single section of biofilm, the sessile microbial activity, for example, can vary across and down the cross-section depending upon these factors. It is believed that the measured fluorogenic agent response can provide a sum total of the response of planktonic and sessile microbiological organisms in the entire system which are in contact with the membrane separation feed stream that contains the fluorogenic agent. Therefore, even if the level of microbial activity is unusually high in a small section of the membrane separation system, but low everywhere else, the fluorogenic agent response may be low. In this regard, it is believed that the method of the present invention can detect the average microbiological organism activity of the system.

In general, the fluorogenic agent added to the membrane system must be a molecule or species that undergoes a change in its fluorescent signal upon interaction with a broad population of microbiological organisms. It should be appreciated by those skilled in the art that environmental factors, such as pH and temperature, may affect the fluorescent signal and should be accounted for and corrected accordingly. Suitable fluorogenic agents, include, but are not limited to, acetic acid ester of pyrene 3,6,8-trisulfonic acid;
carboxyfluorescein diacetate,
3-carboxyumbelliferyl β-D-galactopyranoside;
3-carboxyumbelliferyl β-D-glucuronide;
9H-(1,3-dichloro-9,0-dimethylacridine-2-one-7-yl), D-glucuronide;
9H-(1,3-dichloro-9,9-dimethylacridin-2-one-7-yl);
resorufin β-D-galactopyranoside;
fluorescein di- β-D-galactopyranoside;
fluorescein di- β-D-glucuronide;
resorufin β-D-glucuronide;
fluorescein diphosphate;
7-hydroxy-3H-phenoxazin-3-one 10-oxide (hereinafter "resazurin");
7-hydroxy-3H-phenoxazin-3-one 10-oxide, sodium salt (hereinafter "resazurin, sodium salt");
4-methylumbelliferyl phosphate ("4MUP");
4-methylumbelliferyl β-D-glucuronide;
pyranine phosphate;
pyrene 3,6,8-trisulfonic acid 1-phosphate; and
all like fluorogenic agents, derivatives and combinations thereof.

The preferred fluorogenic agents include resazurin, 4MUP, pyranine phosphate and combinations thereof. Resazurin is the most preferred fluorogenic agent.

It should be appreciated by those skilled in the art that the fluorogenic agents are either commercially available (for example, resazurin, sodium salt is available from ALDRICH® of Milwaukee, Wis.) or capable of being synthesized using procedures reported in the literature (for example, as is the case with pyranine phosphate).

The fluorogenic agent is added to the feed stream in an amount which is capable of determining microbial activity. In an embodiment, an effective amount of fluorogenic agent ranges from about 5 ppt to about 500 ppm, preferably from about 0.5 ppb to about 5 ppm, and more preferably from about 5 ppb to about 500 ppb. When the salt form of the agent (e.g., resazurin, sodium salt) is added to the industrial water system, the calculation of ppm is based on the active amount of the fluorogenic agent present.

The cost of the fluorogenic agent also places a practical upper limit on the amount of fluorogenic agent added to the system. Additional factors influencing fluorogenic agent addition to the system include the type of fluorogenic agent, the amount of liquid continuously lost and replenished within the membrane separation system and the type of fluids contained within the membrane separation system.

In an embodiment, it is preferred that the fluorogenic agent of the present invention meet the following criteria:

1. Not be adsorbed by the membrane in any appreciable amount;
2. Not degrade the membrane or otherwise hinder its performance or alter its composition;
3. Be detectable on a continuous or semi-continuous basis and susceptible to concentration measurements that are accurate, repeatable and capable of being performed on feedwater, concentrate water, permeate water or other suitable media or combinations thereof;
4. Be substantially foreign to the chemical species that are normally present in the water of the membrane separation systems in which inert tracers may be used;
5. Be substantially impervious to interference from, or biasing by, the chemical species that are normally present in the water of membrane separation systems in which inert tracers may be used;
6. Be substantially impervious to any of its own potential specific or selective losses from the water of membrane separation systems, including selective permeation of the membrane;
7. Be compatible with all treatment agents employed in the water of the membrane separation systems in which inert tracers may be used, and thus in no way reduce the efficacy thereof;
8. Be compatible with all components of its formulation; and
9. Be relatively nontoxic and environmentally safe, not only within the environs of the water or the membrane separation system in which it may be used, but also upon discharge therefrom.

It should be appreciated that the present invention only requires a single fluorogenic species to exist with the introduction of the fluorogenic agent as long as that species is reacted and can be measured between the point of introduction and the point of measurement.

In an embodiment, the fluorogenic agents suitable for use in the instant claimed process must have a detectable fluorescent signal prior to their reacting with the microorganisms and also must have a different fluorescent signal after they have reacted with the microorganisms.

It is believed, without intending to be bound thereby, that enzymes synthesized by the living microbiological organisms in the membrane separation can act upon the fluorogenic agents. This activity causes a change in the fluorescent signal of the fluorogenic agent. By monitoring the fluorescent signal, microbiological activity during membrane separation can be monitored. As previously discussed, the methods of the present invention are capable of monitoring microbiological activity from both planktonic and sessile populations, in contrast to methods known in the art.

In an embodiment, the fluorogenic agent can be fed either by itself or in combination with another membrane separation agent, such as an inert fluorescent tracer, a treatment agent, such as scale and corrosion inhibitors, like agents and combinations thereof. By "treatment chemicals and/or agents" is meant without limitation treatment chemicals that enhance membrane separation process performance, antiscalants that retard/prevent membrane scale deposition, antifoulants that retard/prevent membrane fouling, biodispersants and microbial-growth inhibiting agents, such as biocides and cleaning chemicals that remove membrane deposits.

The fluorescent signals of the fluorogenic agent, the reacted fluorogenic agent and the inert fluorescent tracer material can be measured in a variety of different and suitable ways, such as by commercially available fluorometers. Fluorometers with suitable filters may be used to measure the fluorescent signal or signals derived from the fluorogenic agent, the reacted fluorogenic agent and/or the inert fluorescent tracer.

Measuring the fluorescent signal of both the fluorogenic agent and the reacted fluorogenic agent is a known procedure to someone skilled in the art of fluorometry. For example, the fluorescent properties of the fluorogenic agent resazurin are well known both in its unreacted state and in its reacted "resorufin" state. In a preferred embodiment, the membrane separation system is sampled at locations such that grab samples do not have to be taken for measurements via the fluorometers. When the sampling components for the fluorometers are located within the membrane separation system, this type of sampling is typically referred to as an in-line measurement.

An in-line measurement is one that is taken without interrupting the flow of the system being measured. Because the sample components for the fluorometer(s) are positioned in-line when conducting an in-line measurement, the sample they are monitoring accurately reflects the entire membrane separation system and, as such, the information gleaned from conducting this method accurately reflects both the planktonic and sessile microbiological organism populations. In-line measurement overcomes the problems associated with grab sampling and the need to remove a sample from the aqueous stream for later testing. Also, the reacted and unreacted forms of the fluorogenic agents are tested on a real-time basis, wherein an almost instantaneous fluorescence reading of the two fluorogenic agents will provide an indication of microbial activity.

Notwithstanding the fact that in-line measurement is the preferred way of conducting the method of the instant claimed invention, it is possible to conduct the method of the instant claimed invention using a grab sampling technique suitable to secure samples of the industrial water system. If a grab sampling technique is used, a mechanism should necessarily be provided to convey the grab sample to the fluorometer in a reasonable length of time such that the data received from the fluorometer accurately reflects the current microbial growth status of the membrane separation system.

Examples of fluorometers that may be used in the practice of this invention include the TRASAR® 350 and TRASAR® 8000 fluorometers (available from Ondeo Nalco Company of Naperville, Ill.); the Hitachi F-4500 fluorometer (available from Hitachi through Hitachi Instruments Inc. of San Jose, Calif.); the JOBIN YVON FluoroMax-3 "SPEX" fluorometer (available from JOBIN YVON Inc. of Edison, N.J.); and the Gilford Fluoro-IV spectrophotometer or the SFM 25 (available from Bio-tech Kontron through Research Instruments International of San Diego, Calif.). It should be appreciated by those skilled in the art that the fluorometer list is not comprehensive and is intended only to show examples of fluorometers. Other commercially available fluorometers and modifications thereof can also be used in this invention.

In an embodiment, a fluorescent signal ratio is used as an indication of microbial activity and thus an indication of biofouling during membrane separation. By calculating the ratio as opposed to simply measuring an absolute value of fluorescent signals, information is obtained that is independent of fluorogenic agent concentration. In another embodiment, the ratio can increase the sensitivity due to the fact that the microbiological organisms convert fluorogenic reagent to reacted fluorogenic agent with the ratio increase being due to both the decrease in the fluorescent signal of the unreacted fluorogenic agent and increase in the fluorescent signal of the reacted fluorogenic agent (e.g., the product).

The ratio of the fluorescent signal of the fluorogenic agent to the fluorescent signal of the reacted fluorogenic agent is:

$$\text{ratio} = \frac{\text{fluorescent signal of reacted fluorogenic agent}}{\text{fluorescent signal of fluorogenic agent}}$$

The ratio is a unitless number. The ratio can be calculated manually or with a calculator or with a computer program. For ease of use, it is preferable that the ratio be calculated using an appropriate computer program such that a record of the ratio can be continuously calculated at set intervals. The rate of change of the ratio can then be used to determine the rate of increase of biofouling.

In an embodiment, the inert fluorescent tracer material is used to determine the concentration of fluorogenic agent present and by knowing that concentration it is possible to operate the system so that a desired level of fluorogenic agent is fed accurately. See U.S. Pat. Nos. 4,783,314; 4,992,380 and 5,041,386, which are incorporated herein by reference.

The meaning of the term "inert", as used herein, is that an inert fluorescent tracer is not appreciably or significantly affected by any other chemistry in the system, or by the other system parameters such as microbiological activity, biocide concentration and scale inhibitor concentration. To quantify what is meant by "not appreciably or significantly affected", this statement means that an inert fluorescent compound has no more than a 10% change in its fluorescent signal, under conditions normally encountered in industrial water systems. Conditions normally encountered in industrial water systems are known to people of ordinary skill in the art of industrial water systems.

Inert fluorescent tracer materials suitable for use with the fluorogenic agents that are used in the instant claimed invention must have the property of having their unique fluorescent signal be detectably different than the fluorescent signals of the fluorogenic agent. This means that the fluorescent signal of the fluorogenic agent and the fluorescent signal of the reacted fluorogenic agent must both be detectably different than that of the inert fluorescent tracer material.

Suitable inert fluorescent tracer materials are the mono-, di- and tri-sulfonated naphthalenes, including their known water-soluble salts; and the known sulfonated derivatives of pyrene, such as 1,3,6,8-pyrenetetrasulfonic acid, along with the known water-soluble salts of all of these materials, and Acid Yellow 7 (Chemical Abstract Service Registry Number 2391-30-2, for 1H-Benz(de) isoquinoline-5-sulfonic acid, 6-amino-2,3-dihydro-1,3-dioxo-2-p-tolyl-, monosodium salt (8CI)).

In an embodiment, the present invention includes a controller (not shown) to monitor and/or control the operating condition or performance of the membrane separation system based on the measurable fluorescence of the fluorogenic agent, reacted fluorogenic agent, and/or the inert fluorescent tracer. In this regard, biofouling is monitored in the membrane separation system by measuring the change in the signal of the fluorogenic agent or the reacted fluorogenic agent with respect to the signal of the inert fluorescent tracer and then comparing the resultant ratio to the corresponding ratio in the feed stream or the corresponding ratio at time zero, i.e., right after the membrane has been cleaned. The controller can be configured and/or adjusted in a variety of different and suitable ways.

For example, the controller can be in contact with the detection device (not shown) to process the detection signal (e.g., filter noise from the signal) in order to enhance the detection of the fluorescent signal(s) derived from the fluorogenic agent, reacted fluorogenic agent and/or the inert fluorescent tracer. Further, the controller can be adjusted to communicate with other components of the membrane separation system. The communication can be either hard wired (e.g., electrical communication cable), a wireless communication (e.g., wireless RF interface), a pneumatic interface or the like.

In this regard, the controller can be utilized to control the performance of membrane separation by determining the optimal amount of biocontrol treatment needed. "Biochemical treatment" includes biocides, biocontrol agents, biocontrol methods and combinations thereof. For example, the controller can communicate with a feed device (not shown) in order to control various biofouling control chemicals or biofouling control devices or process parameters. In an embodiment, the controller is capable of adjusting the feed rate of biocontrol agent(s) added to the feed stream during membrane separation based on the fluorescence of the fluorogenic agent and reacted fluorogenic agent that are measured. In another embodiment, the addition of biocontrol agents are controlled based on the determination of the ratio of reacted fluorogenic agent to fluorogenic agent. In another embodiment, the addition of biocides are controlled based on the determination of the rate of change of ratio of reacted fluorogenic agent to fluorogenic agent.

A real-time determination of the fluorescence of the fluorogenic agent(s) enables immediate evaluation of the microbial activity as well as the efficiency of the current biocontrol agent dosage and/or the need for an additional feed of the biocontrol agent. Real-time determination of biological activity enables the process to add biocontrol agents on an as needed basis. Adding excess biocontrol agents, greater than what is needed to control the microbial activity is avoided when the biofouling condition is accessed on a real-time basis. Thus, the use of biocontrol agents can be administered at determined effective levels, which results in the correct amount being used. Additionally, the effectiveness of a biocontrol agent feed can be evaluated on a real-time basis and the dosage can be increased or decreased depending upon the real-time reading.

When the method of the instant claimed invention is conducted in the presence of biocontrol agents, certain adjustments have to be made. People of ordinary skill in the art know what biocides are used in membrane separation systems. In an embodiment, biocides added in response to unacceptable levels of microbial activity include oxidizing biocides, non-oxidizing biocides and combinations thereof.

Suitable oxidizing biocides include, but are not limited to:
BCDMH (92.5%, 93.5%, 98%), which is either 1,3-dichloro-5,5-dimethylhydantoin and 1-bromo-3-chloro-5,5-dimethyl hydantoin (CAS Registry #16079-88-2) or a mixture thereof, bleaches, including stabilized bleaches;

bromine, including stabilized bromine;

calcium hypochlorite (CAS Registry #7778-54-3) "Cal Hypo" (68%);

chlorine, including stabilized chlorine (8.34%);

$H_2O_2$/PAA (21.7%/5.1%) which is hydrogen peroxide (CAS Registry #7722-84-1)/peracetic acid (CAS Registry #79-21-0);

hypobromite;

hypobromous acid;

iodine;

organobromines;

NaBr (42.8%, 43%, 46%) which is sodium bromide;

NaOCl (10%, 12.5%) which is sodium hypochlorite (CAS Registry #7681-52-9);

and mixtures thereof.

Suitable non-oxidizing biocides include, but are not limited to,

ADBAC Quat (10%, 40%(CAS Registry #68391-0-5), 80%)—alkyl dimethyl benzyl ammonium chloride, also known as "quat";

ADBAC quat(15%)/TBTO (tributyl tin oxide 5%);

ADBAC(12.5%)/TBTO (2.5%), (ADBAC Quat/bis tributyl tin oxide) (CAS Registry #56-35-9);

carbamates (30%), of formula $T_2NCO_2H$, where $T_2$ is a $C_1$–$C_{10}$ alkyl group; copper sulfate (80%);

DBNPA (20%, 40%), which is 2,2-dibromo-3-nitrilopropionamide (CAS Registry #10222-01-2);

DDAC Quat (50%) which is didecyl dimethyl ammonium chloride quat;

DPEEDBAC Quat (1%) which is (2-(2-p-(diisobutyl) phenoxy)ethoxy)ethyl dimethyl, dimethyl benzyl;

glutaraldehyde (15%, 45%), CAS Registry #111-30-8;

glutaraldehyde (14%)/ADBAC quat (2.5%);

HHTHT—hexahydro-1,3,5-tris (2-hydroxyethyl)-5-triazine (78.5%); isothiazolones (1.5%, 5.6%)—a mixture of 5-chloro-2-methyl-4-isothiazoline-3-one (CAS Registry #26172-55-4) and 2-methyl;-4-isothiazoline-3-one (CAS Registry #2682-20-4);

MBT (10%)—methylene bis thiocyanate;

polyquat (20%, 60%), a polymeric quaternary compound; polyamines and salts thereof—polymeric amine compounds;

terbutylazine (4%, 44.7%)—2-(tert-butylamino)-4-chloro-6-ethylamino-5-triazine (CAS Registry #5915-41-3);

TMTT (24%)—tetramethylthiuram disulfide;

and mixtures thereof.

Other types of biocontrol agents include bio-dispersants, bio-detergents, chaotropic agents, surfactants, chelating agents, enzymatic cleaners, and other chemicals that kill bacteria or interfere with bacterial and EPS attachment and bacteria colonization processes.

Biocontrol methods, such as mechanical means to disrupt biofilm integrity including ultrasound, electric fields, air backwashes, etc. can also be used.

Since membrane systems have very short holding times, the interference of biocontrol agents with the fluorogenic agent does not pose any problems in most practical applications by simply not applying the biocontrol agent during the introduction of the fluorogenic agent. In practice, the biocontrol agent may only be added intermittently.

Although membrane separation systems are often employed for the purification of water, or the processing of aqueous streams, the systems of the present invention are not limited to the use of an aqueous influent. In an embodiment, the influent may be another fluid, or a combination of water and another fluid. The operational principles of membrane separation systems and processes of the present invention are not so governed by the nature of the influent that the present invention could not be employed with influents otherwise suitable for water purification in a given membrane separation system. The descriptions of the invention above that refer to aqueous systems are applicable also to nonaqueous and mixed aqueous/nonaqueous systems.

The foregoing descriptions of the present invention at times refer specifically to aqueous influents and effluents, and the use of an aqueous system for describing a membrane filtration system and the operation of the present invention therein is exemplitive. A person of ordinary skill in the art, given the disclosures of the present specification, would be aware of how to apply the foregoing descriptions to non-aqueous membrane filtration systems.

It should be appreciated that the present invention is applicable to all industries that can employ membrane separation processes. For example, the different types of industrial processes in which the method of the present invention can be applied generally include raw water processes, waste water processes, industrial water processes, municipal water treatment, food and beverage processes, pharmaceutical processes, electronic manufacturing, utility operations, pulp and paper processes, mining and mineral processes, transportation-related processes, textile processes, plating and metal working processes, laundry and cleaning processes, leather and tanning processes, and paint processes.

In particular, food and beverage processes can include, for example, dairy processes relating to the production of cream, low-fat milk, cheese, specialty milk products, protein isolates, lactose manufacture, whey, casein, fat separation, and brine recovery from salting cheese. Uses relating to the beverage industry including, for example, fruit juice clarification, concentration or deacidification, alcoholic beverage clarification, alcohol removal for low-alcohol content beverages, process water; and uses relating to sugar refining, vegetable protein processing, vegetable oil production/processing, wet milling of grain, animal processing (e.g., red meat, eggs, gelatin, fish and poultry), reclamation of wash waters, food processing waste and the like.

Examples of industrial water uses as applied to the present invention include, for example, boiler water production, process water purification and recycle/reuse, softening of raw water, treatment of cooling water blow-down, reclamation of water from papermaking processes, desalination of sea and brackish water for industrial and municipal use, drinking/raw/surface water purification including, for example, the use of membranes to exclude harmful microorganisms from drinking water, polishing of softened water, membrane bio-reactors, mining and mineral process waters.

Examples of waste water treatment applications with respect to the inert tracer monitoring methods of the present invention include, for example, industrial waste water treatment, biological waste treatment systems, removal of heavy metal contaminants, polishing of tertiary effluent water, oily waste waters, transportation related processes (e.g., tank car wash water), textile waste (e.g., dye, adhesives, size, oils for wool scouring, fabric finishing oils), plating and metal working waste, laundries, printing, leather and tanning, pulp and paper (e.g., color removal, concentration of dilute spent sulfite liquor, lignon recovery, recovery of paper coatings), chemicals (e.g., emulsions, latex, pigments, paints, chemical reaction by-products), and municipal waste water treatment (e.g., sewage, industrial waste).

Other examples of industrial applications of the present invention include, for example, semiconductor rinse water processes, production of water for injection, pharmaceutical water including water used in enzyme production/recovery and product formulation, and electro-coat paint processing.

EXAMPLES

The following examples are intended to be illustrative of the present invention and to teach one of ordinary skill how to make and use the invention. These examples are not intended to limit the invention or its protection in any way.

Example 1

A test membrane system was used to demonstrate the monitoring of biofilm growth on a reverse osmosis membrane. The system was a test unit (SEPA CF membrane cell) manufactured by Osmonics. The unit included a new (i.e. clean) flat sheet of membrane measuring 3.5 inches×5 inches. Feed water at 360 psig was forced into the feed channel of the membrane housing at about 150 millimeters per minute (ml/min). As the feed water traveled across the membrane towards the reject exit channel, pressure forced the water molecules through the membrane into the permeate channel at about 15 ml/min. Exit water on the reject channel was about 360 psig. The pressure drop reported was the pressure at the feed channel minus the pressure at the reject channel.

The permeate flow as percentage of feed flow was 10%, which is typical for a reverse osmosis membrane element. The feed water had a conductivity of 3.9 milli-Siemens/cm. The permeate water had a conductivity of 0.2 milli-Siemens/cm. The operating temperature was 78° F. and the pH was 7.

In the test membrane system, a seeding of bacteria was performed and, thus, the microbial biofouling began almost immediately after seeding. The experiment was run for a period of about 90 to 170 hours after seeding. Variables affected by fouling (e.g., permeate flow, pressure differential between feed channel and reject channel, and permeate conductivity) were measured. The surface microbial enumeration of the membrane was performed at the end of the run.

To demonstrate the use of the fluorogenic agent, a solution of about 2 ppm (parts per million) resazurin was fed at 3 ml/min into the feed stream (which had a flow rate of about 150 ml/min) before it entered the membrane feed channel for a period of about five minutes. The concentration of the resazurin after mixing with the feed water was about 40 ppb (parts per billion).

The fluorescence measurement was conducted in the reject stream with an on-line fluorometer (Nalco TRASAR® 350) and with a bench-top fluorometer (Jobin Yvon Spectrometer Fluoro-MAX 3). The residence time of the resazurin chemical in the membrane system was on the order of about one minute. The fluorescence measurement reached a steady state generally in about three minutes after commencement of the resazurin feed. The 5-minute feeding and measurement of the fluorogenic agent was repeated periodically during the course of the experiment.

TABLE 1

| Time (Hr) | TRASAR 350 (Ratio) | Permeate flow (ml/min) | Pressure drop (inch water) | Permeate conductivity (milli-Siemen/cm) | Microbial enumeration on membrane* (cfu/cm$^2$) |
|---|---|---|---|---|---|
| 1 | 1.0 | 15 | 0.8 | 0.17 | — |
| 28 | 1.4 | 13 | 0.8 | 0.13 | — |
| 54 | 1.9 | 10 | 0.9 | 0.16 | — |
| 72 | 2.0 | 7 | 0.9 | 0.20 | — |
| 144 | 2.3 | 3 | 1.7 | 0.29 | 4 × 10$^8$ |

*No microbial activity on the membrane surface at the beginning of the experiment.

TABLE 2

| Time Hr | TRASAR 350 | | | Fluoro-MAX 3 | | |
|---|---|---|---|---|---|---|
| | Ratio | 583 nm Rf | 634 nm Rz | Ratio | 583 nm Rf | 634 nm Rz |
| 1 | 1.0 | 39 | 41 | 1.0 | 24300 | 23900 |
| 28 | 1.4 | 70 | 50 | 1.5 | 44100 | 29600 |
| 54 | 1.9 | 96 | 51 | 2.0 | 59600 | 29500 |
| 72 | 2.0 | 110 | 55 | 2.2 | 71600 | 33100 |
| 144 | 2.3 | 133 | 58 | 2.4 | 73200 | 30900 | sodium citrate. A field deposit from a reverse osmosis membrane unit was inoculated in the medium and allowed to grow. The solution was then incubated at 30° C. in a flask shaker at a speed of about 200 revolutions per minute (rpm). Aliquots of sample were collected using a sterile pipette at different time intervals. Samples collected from each time point were analyzed for optical density, microbial enumeration (at 8, 12, and 24 hr) and allowed to react with resazurin. Optical density was performed with absorbance at 600 nm using a Cintra Spectrophotometer. Microbial enumeration was performed with spread plate on TGE agar after eight serial dilutions of 1:10 with a sterile phosphate buffer solution. In resazurin reaction tests, samples were dosed with 50 ppb of resazurin. Aliquots of a 3.5 ml sample were retrieved at reaction times of 1, 2, 3, 5, 10 minutes and then filtered through a 0.22 micrometer sterile syringe filter to stop the reaction. These reacted samples were subsequently measured for fluorescence of resazurin and resorufin. Response of resazurin was judged by the fluorescence ratio of resorufin to resazurin. Fluorescence measurements were conducted at excitation wavelength 550 nm and emission wavelengths 583 nm and 634 nm, using a Horiba Jobin Yvon fluorometer (model FluoroMax-3) with slit width 2.5 nm (excitation) and 2.5 nm (emission). resazurin had a peak fluorescence at 634 nm and resorufin at 583 nm.

TABLE 3

| Microbial Growth with Time (hour) | Fluorescence ratio of resorufin to resazurin at each reaction time for each sample (Intensity) | | | | | Optical density (absorbance) 600 nm | Viable plate count cfu/ml |
|---|---|---|---|---|---|---|---|
| | t = 1 min | t = 2 min | t = 3 min | t = 5 min | t = 10 min | | |
| 0 | 1.00 | 0.93 | 0.94 | 0.89 | 1.00 | 0.0001 | |
| 4 | 1.29 | 1.42 | 0.95 | 0.94 | 1.31 | | |
| 6 | 1.03 | 1.27 | 0.96 | 1.20 | 0.97 | 0.0020 | |
| 8 | 1.17 | 1.14 | 1.17 | 1.18 | 1.29 | 0.0094 | 3.10E+06 |
| 10 | 1.25 | 1.20 | 1.30 | 1.33 | 1.29 | 0.0162 | |
| 12 | 1.55 | 1.52 | 1.61 | 1.58 | 1.79 | 0.0629 | 3.90E+07 |
| 24 | 2.81 | 3.11 | 3.22 | 3.50 | 3.75 | 0.4261 | 2.40E+09 |

As shown above in Tables 1 and 2, the Ratio of the fluorescence of the reacted fluorogenic agent (e.g., resorufin (Rf) to the fluorescence of the fluorogenic agent (e.g., resazurin (Rz)) increased with microbial growth and accumulation during the course of the experiment. It should be appreciated that the values for Rf and Rz in Tables 1 and 2 represent an intensity of the fluorescence signal as measured which corresponds to an amount of the reacted fluorogenic agent and the fluorogenic agent. Furthermore, Tables 1 and 2 demonstrate the existence of a correlation between the Ratio and the membrane separation performance variables measured by permeate flow, pressure drop and permeate conductivity.

Example 2

A batch test was performed to quantify the reaction between microbial activity and resazurin, a fluorogenic agent. The test was conducted in a minimal medium solution containing 100 ppm glycerol, 7 grams/liter (g/L) $K_2HPO_4$, 0.1 g/L $MgSO_4 \cdot 7H_2O$, 1 g/L $(NH_4)_2 \cdot SO_4$ and 0.5 g/L As demonstrated in Table 3, the fluorescence ratio of resorufin to resazurin increased as microbial growth increased as indicated by optical density (absorbance 600 nm) and viable cell count. The ratio also increased as reaction time between the sample and resazurin increased, especially when microbial density was about 10$^6$ cfu/ml or above. The results show that resazurin is responsive to the microbial growth of a membrane biofilm.

Example 3

A batch test was performed to quantify the relationship between a resazurin dose concentration and its response to different levels of microbial density during microbial growth. The test was conducted in a minimal medium solution inoculated with field reverse osmosis (RO) membrane deposit as described in Example 2. The solution was incubated at 30° C. in a flask shaker at a speed of 200 rpm. Aliquots of sample were collected using a sterile pipette at different time intervals. Samples collected from each time point were analyzed for optical density, microbial enumeration (except time zero and 2 hours) and allowed to react with resazurin. Optical density and microbial enumeration were performed using the same methods described in Example 2.

In the resazurin reaction test, samples were dosed with 50 ppb, 500 ppb and 5000 ppb of resazurin. Aliquots of 3.5 ml samples were retrieved after 1 minute reaction. These reacted samples were subsequently measured for fluorescence of resazurin and resorufin. The response of resazurin was evaluated by the fluorescence ratio of resorufin to resazurin. The method of fluorescence measurements is described above in Example 2.

Membrane samples were taken periodically for sessile microbial enumeration and resazurin response test. A membrane sample was soaked in a sterile phosphate buffer solution (PBS) in a 45 ml test tube for a 5 minute sonication. An aliquot of bulk from the sonicated sample was then diluted with sterile PBS in eight serial dilutions of 1:10 before plated on TGE agar plate. The viable plate count represented sessile cell density from the RO membrane,

TABLE 4

| Microbial growth time | Fluorescence ratio of resorufin to resazurin at each dose concentration | | | Relative change of ratio (Rf/Rzt-Rf/Rzo) | Optical density (Absorbance) | Viable plate count |
|---|---|---|---|---|---|---|
| (hr) | 0.05 ppm | 0.5 ppm | 5 ppm | 50 ppb | OD600 | cfu/ml |
| 0 | 0.878 | 0.761 | 0.400 | | 0.0013 | |
| 2 | 1.107 | 0.766 | 0.413 | 0.229 | 0.0013 | |
| 4 | 1.241 | 0.927 | 0.445 | 0.363 | 0.0013 | 1.40E+05 |
| 6 | 1.217 | 0.892 | 0.456 | 0.338 | 0.0112 | 2.10E+05 |
| 8 | 1.147 | 0.928 | 0.456 | 0.269 | 0.0029 | 4.70E+05 |
| 10 | 1.244 | 0.930 | 0.476 | 0.366 | 0.0052 | 2.30E+06 |
| 14 | 1.346 | 0.921 | 0.433 | 0.468 | 0.0223 | 1.90E+07 |
| 25 | 2.560 | 1.520 | 0.676 | 1.682 | 0.2185 | 2.50E+09 | where Rf=resorufin; Rz=resazurin; Rf/Rz=ratio of resorufin to resazurin;

Rf/Rzt=ratio of resorufin to resazurin at time t (t=2, 4, 6, 8, 10, 14, 25 hours);

and Rf/Rzo=ratio of resorufin to resazurin at time zero.

TABLE 5

| Log Resazurin dose (ppb) | Rz dose (ppb) | Fluorescence ratio of Rf/Rz at different microbial cell density (cfu/ml) | | |
|---|---|---|---|---|
| | | 2.00E+06 | 2.00E+07 | 3.00E+09 |
| 1.70 | 50 | 1.24 | 1.35 | 2.56 |
| 2.70 | 500 | 0.93 | 0.92 | 1.52 |
| 3.70 | 5000 | 0.48 | 0.43 | 0.68 |
| Linear regression | | | | |
| | Slope | −0.38 | −0.46 | −0.94 |
| | Intercept | 1.92 | 2.13 | 4.13 |
| | RSQ | 0.9890449 | 0.99844 | 0.996395936 |

As indicated in Tables 4 and 5, the fluorescence ratio of resorufin to resazurin increased as the resazurin dose decreased at each microbial cell density. Furthermore, the dose of resazurin concentration had a logarithm linear relationship with the fluorescence ratio response in the sample. The change of the ratio also indicated 50 ppb of resazurin was more sensitive to microbial growth than 500 ppb and 5000 ppb of resazurin. The fluorescence ratio of resorufin to resazurin was an order of magnitude more sensitive than the optical density measurement.

Example 4

This test evaluated the correlation between fluorescence response of resazurin and biofilm (sessile cells) on a reverse osmosis (RO) membrane. The test was performed in a 350 ml fed-batch flow cell system. The system was fed with a minimal medium and inoculated with a field RO deposit as described in Example 2. The flow cell was operated at a hydraulic residence time of about 14 hr. A recirculation pump provided mixing to the system at 195 ml/min. RO membrane coupons of 3 inch×1 inch were submerged in the flow cell.

resazurin of 40 ppb was dosed into the sonicated membrane sample in PBS for one minute. An aliquot of sample was then taken to check for fluorescence at the same conditions as described in Example 2. The measured fluorescence ratio of resorufin to resazurin from the sonicated membrane sample represented response to microbial flocs. Another membrane sample was retrieved and soaked in 45 ml PBS in a test tube. The sample was dosed with 40 ppb resazurin for one minute. An aliquot of sample was then collected to measure fluorescence at the same conditions as described in Example 2. The fluorescence ratio associated with this sample represented response to intact biofilms on the RO membrane.

TABLE 6

| Elapsed time (hr) | Sessile cell density on RO membrane Log (cfu/cm$^2$) | Ratio of resorufin to resazurin |
|---|---|---|
| 1 | 3.76 | 0.824 |
| 24 | 7.41 | |
| 48 | 7.43 | 0.888 |
| 72 | 7.73 | 0.888 |
| 96 | 9.09 | 0.992 |
| 168 | 9.11 | 0.955 |
| 174 | 8.37 | 1.051 |

TABLE 7

| Sessile cell density on RO membrane | Ratio of resorufin to resazurin | |
|---|---|---|
| Log (cfu/cm2) | biofilm | flocs |
| 7.43 | 0.888 | 0.993 |
| 7.73 | 0.888 | 1.115 |
| 9.09 | 0.992 | 1.031 |

Table 6 illustrates that response of resazurin increases as sessile cell density from RO membrane increases. Table 7 further demonstrates that the response of resazurin is greater in flocs than intact biofilms.

While the present invention is described above in connection with preferred or illustrative embodiments, these embodiments are not intended to be exhaustive or limiting of the invention. Rather, the invention is intended to cover all alternatives, modifications and equivalents included with its spirit and scope, as defined by the appended claims.

What is claimed is:

1. A method of monitoring biofouling in a membrane separation system including a membrane capable of separating a feed stream into at least a first stream and a second stream comprising the steps of:
   providing a fluorogenic agent; wherein said fluorogenic agent must be capable of passing through the openings in the membranes of the membrane separation system;
   adding the fluorogenic agent to the feed stream;
   providing a fluorometer to detect the fluorescent signal of the fluorogenic agent in at least one of the feed stream, the first stream and the second stream;
   reacting the fluorogenic agent with at least one microorganism within the membrane separation system;
   forming a reacted fluorogenic agent; wherein said reacted fluorogenic agent must be capable of passing through the openings in the membranes of the membrane separation system;
   using the fluorometer to measure the fluorescent signal of at least one of the fluorogenic agent and the reacted fluorogenic agent in at least one of the first stream and the second stream and optionally the feed stream; and
   monitoring biofouling in the membrane separation system based on the change in the signal of the fluorogenic agent, or the reacted fluorogenic agent or a combination of both signals measured.

2. The method of claim 1 wherein the membrane separation system is selected from the group consisting of a cross-flow membrane separation system and a dead-end flow membrane separation system.

3. The method of claim 1 wherein the membrane separation system is selected from the group consisting of reverse osmosis, nanofiltration, ultrafiltration, microfiltration, electrodialysis, electrodeionization, pervaporation, membrane extraction, membrane distillation, membrane stripping, membrane aeration and combinations thereof.

4. The method of claim 1 wherein the membrane separation system is selected from the group consisting of reverse osmosis, nanofiltration, ultrafiltration and microfiltration.

5. The method of claim 1 wherein the fluorogenic agent is selected from the group consisting of acetic acid ester of pyrene 3,6,8-trisulfonic acid; carboxyfluorescein diacetate; 3-carboxyumbelliferyl β-D-galactopyranoside; 3-carboxyumbelliferyl β-D-glucuronide; 9H-(1,3-dichloro-9,0-dimethylacridine-2-one-7-yl), D-glucuronide; 9H-(1,3-dichloro-9,9-dimethylacridin-2-one-7-yl); resorufin β-D-galactopyranoside; fluorescein di-β-D-galactopyranoside; fluorescein di-β-D-glucuronide; resorufin β-D-glucuronide; fluorescein diphosphate; resazurin; resazurin, sodium salt; 4-methylumbelliferyl phosphate; 4-methylumbelliferyl β-D-glucuronide; pyranine phosphate; pyrene 3,6,8-trisulfonic acid 1-phosphate; and combinations thereof.

6. The method of claim 1 wherein the fluorogenic agent is selected from the group consisting of resazurin, 4-methylumbelliferyl phosphate, pyranine phosphate and combinations thereof.

7. The method of claim 1 wherein the fluorogenic agent is resazurin.

8. The method of claim 1 wherein the fluorogenic agent is added into the feed stream in an amount from about 5 ppt to 500 ppm.

9. The method of claim 1 wherein the fluorogenic agent is added into the feed stream in an amount from about 0.5 ppb to 5 ppm.

10. The method of claim 1 wherein the fluorogenic agent is added into the feed stream in an amount from about 5 ppb to about 500 ppb.

11. The method of claim 1 wherein biofouling is monitored by determining a ratio of the fluorescent signal of the reacted fluorogenic agent to the fluorescent signal of the fluorogenic agent in at least one of the first stream and the second stream.

12. The method of claim 11 further comprising determining the rate of change of the ratio of the fluorescent signal of the reacted fluorogenic agent to the fluorescent signal of the fluorogenic agent in at least one of the first stream and the second stream to monitor biofouling.

13. The method of claim 1 further comprising the step of:
   determining the optimal amount of biocontrol treatment based on the change in the signal of the fluorogenic agent, or the reacted fluorogenic agent, or a combination of both signals measured; and
   applying the optimal amount of biocontrol treatment to the membrane separation system.

14. The method of claim 13 wherein the biocontrol treatment is selected from the group consisting of biocides, biocontrol agents, biocontrol methods and combinations thereof.

15. The method of claim 14 wherein the biocides are selected from the group consisting of oxidizing biocides, non-oxidizing and combinations thereof.

16. The method of claim 14 wherein the biocontrol agents are selected from the group consisting of bio-dispersants, bio-detergents, chaotropic agents, surfactants, chelating agents, enzymatic cleaners and combinations thereof.

17. The method of claim 14 wherein the biocontrol methods are selected from the group consisting of ultrasound, electric fields and air backwashes.

18. The method of claim 1 wherein the microorganisms are selected from the group consisting of planktonic microorganisms, sessile microorganisms and combinations thereof.

19. The method of claim 1 further comprising the addition of an inert fluorescent tracer to the feed stream to monitor biofouling in the membrane separation system based on the change in the signal of the fluorogenic agent or the reacted fluorogenic agent relative to the signal of the inert fluorescent tracer.

* * * * *